(12) United States Patent
Chappa et al.

(10) Patent No.: US 8,496,954 B2
(45) Date of Patent: Jul. 30, 2013

(54) COATING SYSTEMS FOR THE CONTROLLED DELIVERY OF HYDROPHILIC BIOACTIVE AGENTS

(75) Inventors: Ralph A. Chappa, Ham Lake, MN (US); Robert W. Hergenrother, Eden Prairie, MN (US); Shannon A. Wadman, Minneapolis, MN (US); Klaus R. Wormuth, St. Louis Park, MN (US)

(73) Assignee: Surmodics, Inc., Eden Prairie, MN (US)

( * ) Notice: Subject to any disclaimer, the term of this patent is extended or adjusted under 35 U.S.C. 154(b) by 280 days.

(21) Appl. No.: 12/386,469

(22) Filed: Apr. 17, 2009

(65) Prior Publication Data

US 2009/0280155 A1    Nov. 12, 2009

Related U.S. Application Data

(60) Provisional application No. 61/124,675, filed on Apr. 18, 2008.

(51) Int. Cl.
| | | |
|---|---|---|
| *A61F 2/00* | (2006.01) | |
| *A61K 9/50* | (2006.01) | |
| *A61K 47/00* | (2006.01) | |
| *A61K 38/00* | (2006.01) | |
| *A01N 25/00* | (2006.01) | |

(52) U.S. Cl.
USPC ....... 424/423; 427/2.21; 514/772; 514/772.1; 514/1.1

(58) Field of Classification Search
None
See application file for complete search history.

(56) References Cited

U.S. PATENT DOCUMENTS

| | | | |
|---|---|---|---|
| 5,660,854 A | 8/1997 | Haynes et al. | |
| 5,879,713 A | 3/1999 | Roth et al. | |
| 5,980,948 A | 11/1999 | Goedemoed et al. | |
| 6,143,037 A | 11/2000 | Goldstein et al. | |
| 6,214,901 B1 | 4/2001 | Chudzik et al. | |
| 6,228,393 B1 | 5/2001 | DiCosmo et al. | |
| 6,497,729 B1 | 12/2002 | Moussy et al. | |
| 6,503,556 B2 | 1/2003 | Harish et al. | |
| 6,669,980 B2 | 12/2003 | Hansen | |
| 6,673,385 B1 | 1/2004 | Ding et al. | |
| 7,550,443 B2 | 6/2009 | Stucke et al. | |
| 7,550,444 B2 | 6/2009 | Stucke et al. | |
| 2002/0168394 A1 | 11/2002 | Hossainy et al. | |
| 2002/0188037 A1 | 12/2002 | Chudzik et al. | |
| 2003/0064965 A1 | 4/2003 | Richter | |
| 2003/0129130 A1 | 7/2003 | Guire et al. | |
| 2004/0133155 A1 | 7/2004 | Varner et al. | |
| 2005/0019371 A1 | 1/2005 | Anderson et al. | |
| 2005/0037047 A1 | 2/2005 | Song | |
| 2005/0095267 A1 | 5/2005 | Campbell et al. | |
| 2005/0208095 A1 | 9/2005 | Hunter et al. | |
| 2005/0220843 A1 | 10/2005 | DeWitt et al. | |
| 2005/0244459 A1 | 11/2005 | DeWitt et al. | |
| 2005/0261283 A1 | 11/2005 | Sukhatme | |
| 2006/0110428 A1 | 5/2006 | deJuan et al. | |
| 2006/0257451 A1 | 11/2006 | Varner et al. | |
| 2007/0260054 A1 | 11/2007 | Chudzik | |
| 2007/0276473 A1 | 11/2007 | Llanos et al. | |
| 2008/0020045 A1 | 1/2008 | Chappa et al. | |
| 2008/0038354 A1 | 2/2008 | Slager et al. | |
| 2009/0028956 A1 | 1/2009 | Slager et al. | |

FOREIGN PATENT DOCUMENTS

WO    2005/099667    10/2005

OTHER PUBLICATIONS

Agnes et al. poster presented at the 8$^{th}$ PBP World Meeting 2012; Mar. 19-22, 2012; Istanbul, Turkey.*
PCT Search Report for International Application No. PCT/US2009/002418 mailed on Jun. 22, 2010.

* cited by examiner

*Primary Examiner* — Patricia A Duffy
*Assistant Examiner* — Garen Gotfredson
(74) *Attorney, Agent, or Firm* — Kagan Binder, PLLC (57) ABSTRACT

Described are coating systems for the controlled delivery of hydrophilic bioactive agents, for example, from implantable medical devices. The coating systems of the invention comprise (a) a polymeric basecoat layer containing one or more hydrophilic bioactive agents; and (b) an elution-controlling topcoat layer that comprises a poly(ethylene-co-vinyl acetate) copolymer. The elution rate of the hydrophilic bioactive agent can be controlled by varying the vinyl acetate concentration in the elution-controlling topcoat layer.

19 Claims, 1 Drawing Sheet

COATING SYSTEMS FOR THE CONTROLLED DELIVERY OF HYDROPHILIC BIOACTIVE AGENTS

CROSS REFERENCE TO RELATED APPLICATIONS

This application claims priority to U.S. Provisional Application Ser. No. 61/124,675, filed Apr. 18, 2008, and entitled "COATING SYSTEMS FOR THE CONTROLLED DELIVERY OF HYDROPHILIC BIOACTIVE AGENTS", the disclosure of which is incorporated herein by reference.

FIELD

The invention relates to elution-controlling coating systems for the controlled delivery of hydrophilic bioactive agents, for example, from implantable medical devices.

BACKGROUND

Therapeutic benefits can be achieved in some instances by providing a bioactive agent to a specific target tissue, instead of systemically. This is because the effect of the agent on the target tissue can be maximized while the side effects on other tissues can be minimized. Therapeutic benefits can also be achieved by providing a bioactive agent to a subject in a manner that provides controlled release of the bioactive agent. Controlled release of a bioactive agent can allow the concentration of the bioactive agent at the target tissue site to remain at a more consistent therapeutic level.

One technique for providing controlled-release site-specific drug delivery is to use a bioactive agent-eluting coating system disposed on a medical device. The coating can serve to control the rate at which the bioactive agent is eluted. In addition, because the coating is disposed on a medical device and because the medical device can be positioned as desired within the body of a patient, the delivery of the bioactive agent can be site-specific.

Some types of bioactive agents, however, may be difficult to regulate when provided in the form of an bioactive agent-eluting coating system. Notably, it is difficult to regulate the elution rate of hydrophilic bioactive agents from polymeric coating systems. Accordingly, there is a need for polymeric coating systems that can effectively control the elution rate of hydrophilic bioactive agents.

SUMMARY

The invention provides coating systems for the controlled delivery of hydrophilic bioactive agents, for example, from implantable medical devices. In many embodiments, the coating systems of the invention comprise (a) a polymeric basecoat layer containing one or more hydrophilic bioactive agents; and (b) an elution-controlling topcoat layer that comprises a poly(ethylene-co-vinyl acetate) copolymer. Advantageously, the elution rate of the hydrophilic bioactive agent can be controlled by varying the vinyl acetate concentration in the elution-controlling topcoat layer. Typically, as the vinyl acetate concentration in the topcoat layer increases, the elution rate of the hydrophilic bioactive agent from the coating system also increases.

In some embodiments, the elution-controlling topcoat layer comprises poly(ethylene-co-vinyl acetate) copolymer (pEVA) having a vinyl acetate concentration ranging from about 10% to about 50% vinyl acetate, or from about 12% to about 50% vinyl acetate, or from about 15% to about 35% vinyl acetate. The amount of vinyl acetate may be selected, for example, to provide a desired elution rate for the hydrophilic bioactive agent.

In some embodiments, elution-controlling topcoat layer comprises predominately pEVA, for example greater than about 50% wt. pEVA, 60% wt. or greater pEVA, 70% wt. or greater pEVA, 80% wt. or greater pEVA, about 90% wt. or greater pEVA, or about 99% wt. or greater pEVA.

In some embodiments, the basecoat layer comprises (a) a first hydrophobic polymer; (b) a hydrophilic/hydrophobic polymer; (c) optionally a second polymer; and (d) a hydrophilic bioactive agent. In some embodiments, the hydrophilic bioactive agent is in the form of microparticles that are dispersed within the basecoat layer.

In some embodiments, the first hydrophobic polymer is a biostable polymer, for example, selected from the group consisting of poly(alkyl(meth)acrylates) and poly(aromatic (meth)acrylates). One useful first polymer is poly(n-butyl methacrylate) (pBMA). In many embodiments, the second polymer comprises poly(ethylene-co-vinyl acetate) copolymer (pEVA). In some embodiments, the hydrophilic/hydrophobic polymer is biodegradable polymer. Examples include polyethylene glycol block copolymers and polyether ester copolymer. In an exemplary embodiment, the hydrophilic/hydrophobic polymer comprises PEG and PBT.

In some embodiments, the basecoat layer has a thickness ranging from about 1 µm to about 200 µm, more typically ranging from about 1 µm to about 50 µm, and the elution-controlling topcoat layer has thickness ranging up to about 50 µm, or from about 5 µm to about 10 µm.

In some embodiments, the hydrophilic bioactive agent comprises a hydrophilic macromolecule selected from the group consisting of polypeptides (e.g., antibodies or fragments thereof), polynucleotides, and polysaccharides. Typically, the hydrophilic bioactive agents have a molecular weight of about 1000 Da or greater, for example, from about 10,000 Da to about 200,000 Da. In some embodiments, the hydrophilic bioactive agent comprises a Fab fragment.

In another aspect, the invention provides implantable medical devices comprising the coating system of the invention. Examples include implantable intraocular device such as eye coils. In yet another aspect, the coating system of the invention is in the form of an implant.

In yet another aspect, the invention provides a method for preparing a coating system for the controlled release of a hydrophilic bioactive agent, the method comprising the steps of: (a) providing a basecoat coating composition comprising a basecoat polymer and at least one hydrophilic bioactive agent;

(b) disposing the coating composition on the surface of a substrate to form a basecoat layer; (c) providing a topcoat composition comprising poly(ethylene-co-vinyl acetate) copolymer; and (d) disposing the topcoat composition over at least a portion of the basecoat layer to form the coating system.

In some embodiments, the step of disposing the coating composition comprises spraying the coating composition on the surface of the substrate. The step of disposing the topcoat composition may also comprises spraying the topcoat composition on the surface of the basecoat.

DETAILED DESCRIPTION

The embodiments of the invention described herein are not intended to be exhaustive or to limit the invention to the precise forms disclosed in the following detailed description. Rather, the embodiments are chosen and described so that others skilled in the art can appreciate and understand the principles and practices of the invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention provides coating systems for the controlled delivery of hydrophilic bioactive agents from implantable medical devices. In many embodiments, the coating systems of the invention comprise (a) a polymeric basecoat layer containing one or more hydrophilic bioactive agents; and (b) an elution-controlling topcoat layer that comprises a poly (ethylene-co-vinyl acetate) copolymer. Advantageously, the elution rate of the hydrophilic bioactive agent can be controlled by varying the vinyl acetate concentration in the topcoat comprising a poly(ethylene-co-vinyl acetate) copolymer. As the amount of vinyl acetate in the poly(ethylene-co-vinyl acetate) copolymer increases, the elution rate of the hydrophilic bioactive agent from the coating system also increases. This relationship allows the elution rate of the hydrophilic bioactive agent from the coating system to be controlled by proper selection of the vinyl acetate concentration in the copolymer.

In some embodiments, the coating system of the invention is present in the form of a coating on the surface of an implantable medical device (examples are which are provided herein). The coating system can also be in other forms. For example, the coating system can be formed within a medical device, such as within an inner space (e.g., a lumen) of a device, with the device arranged so that the bioactive agent can be released through a part of the device, such as an aperture or a membrane that is associated with the device, and through which the bioactive agent can pass.

In another form, the coating system can be fabricated as an implant itself. In this case, the coating system is in the form of an implant, such as a filament, coil, or prosthesis. The coating system in the form of an implant can serve as reservoir for release of the hydrophilic bioactive agent, or may also include some structure that (in addition to its drug releasing capability) can be placed in a subject to provide a mechanical feature.

Generally, the coating system of the invention is configured for placement in contact with body tissue or fluid in which the hydrophilic bioactive agent becomes released from the coating system and available to a subject. The release of the bioactive agent can be site specific, and used to treat a medical condition.

The various elements of the coating systems of the invention will now be described in detail.

Basecoat Layer:

Coating systems of the invention comprise a polymeric basecoat layer that contains one or more hydrophilic bioactive agents. The basecoat layer functions as a reservoir for the one or more hydrophilic bioactive agents that are present in the coating system. When implanted in a patient, the one or more hydrophilic bioactive agents elute from the basecoat layer through the topcoat layer in order to treat a medical condition.

In many embodiments, the basecoat layer comprises one or more polymeric materials that are capable of forming a coated layer on an implantable medical device.

In exemplary embodiments of the invention, the basecoat layer comprises (i) a first hydrophobic polymer (e.g., pEVA); (ii) a polymer comprising hydrophobic and hydrophilic segments (e.g., PEG/PBT polymers); (iii) optionally, a second polymer (e.g., pBMA); and (iv) a hydrophilic bioactive agent. In many embodiments, the hydrophilic bioactive agent is in the form of a plurality of microparticles that are dispersed within the basecoat layer. Coatings of this type are described, for example, in U.S. Patent Application Publication No. US 2008/0038354 (Slager et al.).

First Polymer:

In some embodiments, the polymeric basecoat layer includes a first polymer that is hydrophobic. Hydrophobic polymers are those having no appreciable solubility in water.

In some aspects, the hydrophobic polymer provides desirable properties when the coating composition is provided in certain forms. For example, the hydrophobic polymer can provide one or more properties of durability, compliance, etc., to the basecoat layer. As used herein, the term "durability" refers to the wear resistance of a polymer coating, or the ability of a coating to adhere to an article surface when subjected to forces typically encountered during use (for example, normal force, shear force, and the like). A more durable coating is less easily removed from a substrate by abrasion. A compliant coating is one that it shapes well to the article to which is has been coated and that it can form to the changes in the shape of the article without introducing any substantial physical deformities.

In some aspects the first polymer is a durable and biostable hydrophobic polymer. Various durable and biostable hydrophobic polymer have been described in the art or are commercially available.

In some aspects the first polymer is selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Examples of poly(alkyl(meth)acrylates) include those with alkyl chain lengths from 2 to 8 carbons, inclusive. Exemplary sizes of poly(alkyl(meth)acrylates) are in the range of about 50 kilodaltons to about 1000 kilodaltons, about 100 kilodaltons to about 1000 kilodaltons, about 150 kilodaltons to about 500 kilodaltons, and about 200 kilodaltons to about 400 kilodaltons. One exemplary poly(alkyl(meth)acrylate is poly(n-butyl methacrylate) (pBMA).

Other examples of poly(alkyl(meth)acrylates) include poly (n-butyl methacrylate-co-methyl methacrylate, with a monomer ratio of 3:1, poly(n-butyl methacrylate-co-isobutyl methacrylate, with a monomer ratio of 1:1 and poly(t-butyl methacrylate). Such polymers are available commercially (e.g., from Sigma-Aldrich, Milwaukee, Wis.) with molecular weights ranging from about 150 kilodaltons to about 350 kilodaltons, and with varying inherent viscosities, solubilities and forms (e.g., as slabs, granules, beads, crystals or powder).

Examples of poly(aromatic(meth)acrylates) include poly (aryl(meth)acrylates), poly(aralkyl(meth)acrylates), poly (alkaryl(meth)acrylates), poly(aryloxyalkyl(meth)acrylates), and poly(alkoxyaryl(meth)acrylates). Specific examples of poly(aryl(meth)acrylates) include poly(9-anthracenyl methacrylate), poly(chlorophenyl acrylate), poly (methacryloxy-2-hydroxybenzophenone), poly(methacryloxybenzotriazole), poly(naphthyl acrylate), poly (naphthylmethacrylate), poly-4-nitrophenylacrylate, poly (pentachloro(bromo, fluoro) acrylate) and methacrylate, poly (phenyl acrylate) and poly(phenyl methacrylate). Specific examples of poly(aralkyl(meth)acrylates) include poly(benzyl acrylate), poly(benzyl methacrylate), poly(2-phenethyl acrylate), poly(2-phenethyl methacrylate) and poly(1-pyrenylmethyl methacrylate). Specific examples of poly(alkaryl (meth)acrylates include poly(4-sec-butylphenyl methacrylate), poly(3-ethylphenyl acrylate), and poly(2-methyl-1-naphthyl methacrylate). Specific examples of suitable poly(aryloxyalkyl(meth)acrylates) include poly(phenoxyethyl acrylate), poly(phenoxyethyl methacrylate), poly(polyethylene glycol phenyl ether acrylate) and poly(polyethylene glycol phenyl ether methacrylate) with varying polyethylene glycol molecular weights. Specific examples of poly(alkoxyaryl(meth)acrylates) include poly(4-methoxyphenyl methacrylate), poly(2-ethoxyphenyl acrylate) and poly(2-methoxynaphthyl acrylate).

Acrylate or methacrylate monomers or polymers and/or their parent alcohols are commercially available from Sigma-Aldrich (Milwaukee, Wis.) or from Polysciences, Inc, (Warrington, Pa.).

Also included within the scope of the first polymers are polybutadiene, poly(lactic-co-glycolic acid) (PLGA), pEVA, or blends thereof.

Second Polymer:

In some embodiments, the basecoat layer comprises a blend of a first hydrophobic polymer and one or more second polymers.

In some aspects the polymer that can be blended with the first polymer is poly(ethylene-co-vinyl acetate) (pEVA). For example, the blend can be a combination of poly(n-butyl methacrylate) (pBMA) and poly(ethylene-co-vinyl acetate) (pEVA). Such blends are described in commonly assigned U.S. Pat. Nos. 6,214,901 (Chudzik et al.) and US Publication No. 2002/0188037 A1 (Chudzik et al.).

In some aspects the polymer that can be blended with the first polymer is selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. These blends are described in commonly assigned U.S. Patent Application entitled, "Coating Compositions for Bioactive Agents," U.S. Published Application 2005/0220843 (filed Apr. 6, 2005). Alternatively, these polymers may be used as the first polymer.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. In more specific embodiments, such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Copolymers of ethylene and other alkylenes can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In some cases, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for example it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Diolefin-derived, non-aromatic polymers and copolymers, including those in which the diolefin monomer used to prepare the polymer or copolymer can be derived from monomers such as butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl(meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% wt. In an embodiment, epichlorohydrin content is from about 50% to 100% wt. In an embodiment, the epichlorohydrin-containing polymers have a molecular weight from about 100 kilodaltons to about 300 kilodaltons.

Typically, the first and second polymer components comprise about 10% to about 50% weight of the basecoat layer.
Hydrophilic/Hydrophobic Polymer:

In some aspects of the invention, the basecoat layer comprises a polymer that comprises hydrophilic and hydrophobic portions (i.e., a hydrophilic/hydrophobic polymer).

In some aspects the hydrophilic/hydrophobic polymer is a block copolymer comprising hydrophilic and hydrophobic blocks. The linkages between the blocks may be biodegradable or biostable. The hydrophilic and hydrophobic blocks can be either or both biodegradable or biostable.

Exemplary hydrophilic blocks can be selected from polymer segments formed from monomers such as ethylene glycol, ethylene oxide, vinyl alcohol, propylene oxide, vinyl pyrrolidone, hydroxy ethyl methacrylate, and hydroxy ethyl acrylate.

Exemplary hydrophilic blocks include (PEO), polyvinyl alcohol (PVA), poly(vinyl pyrrolidone) (PVP), polyacrylamide, poly(hydroxy alkyl methacrylate), poly(hydroxy ethyl methacrylate), hydrophilic polyurethane, HYPAN, oriented HYPAN, poly(hydroxy ethyl acrylate), poly(ethyloxazoline), and polyamines (e.g., Jeffamine™).

In some aspects the hydrophilic/hydrophobic polymer comprises a polyalkoxyalkane block. Representative examples of polyalkoxyalkane blocks include poly(ethylene glycol), tetraethylene glycol, triethylene glycol, trimethylolpropane ethoxylate, and pentaeerythritol etholxylate blocks.

Exemplary hydrophilic blocks have a molecular weight of about 100 Da to about 5000 Da, or about 250 Da to about 3500.

In some aspects the hydrophobic blocks include a biodegradable polymeric segment selected from polycaprolactone (PCL), polyvalerolactone (PVL), poly(lactide-co-glycolide) (PLGA), polylactic acid (PLA), polybutyrolactone (PBL), polyglycolide, polypropiolactone (PPL), and polytrimethylene carbonate.

In some aspects the hydrophobic block comprises a poly (alkylene dicarboxylate), such as poly(ethylene terephthalate), poly(butylene terephthalate), poly(butylene-2,6-naphthalate), poly(ethylene-2,6-naphthalate), poly (cyclohexanedimethanol terephthalate), poly(ethylene-co-cyclohexanedimethanol terephthalate), polytrimethylene terephthalate, poly(dimethanol-1,4-cyclohexanedicarboxylate), and polyxylene terephthalate.

Biodegradable polyetherester copolymers can be used as the hydrophilic/hydrophobic polymer. Generally speaking, the polyetherester copolymers are amphiphilic block copolymers that include hydrophilic (for example, a polyalkylene glycol, such as polyethylene glycol) and hydrophobic blocks (for example, polyethylene terephthalate). Specific examples of degradable polymers include poly(ether ester) multiblock copolymers based on poly(ethylene glycol) (PEG) and poly (butylene terephthalate) (PBT) that can be described by the following general structure:

where —$C_6H_4$— designates the divalent aromatic ring residue from each esterified molecule of terephthalic acid, n represents the number of ethylene oxide units in each hydrophilic PEG block, $\chi$ represents the number of hydrophilic blocks in the copolymer, and y represents the number of hydrophobic blocks in the copolymer. The subscript η can be selected such that the molecular weight of the PEG block is between about 300 and about 4000. X and y can be selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure. Examples of these types of multiblock copolymers are described in, for example, U.S. Pat. No. 5,980,948. PEG/PBT polymers are commercially available from Octoplus BV, under the trade designation PolyActive™.

In some aspects the hydrophilic/hydrophobic polymer comprises a hydrophilic backbone and pendent hydrophobic groups. In some aspects the hydrophilic backbone comprises a polysaccharide Exemplary polysaccharides with pendent hydrophobic groups include fatty acid derivatized poly-α (1→4)glucopyranose polymers, such as described in U.S. patent application Ser. No. 11/724,553, filed Mar. 15, 2007 (Chudzik). The polysaccharides can include a level of derivation and pendent hydrophobic groups suitable for use as a second polymer. The linkages between the hydrophilic backbone and the pendent hydrophobic groups can be hydrolytically cleavable and can include ester groups.

The hydrophilic and hydrophobic portions of the second polymer can also be defined in terms of their weight ratios in the polymer. For example, in some aspects, the weight ratio of the hydrophilic portion to the hydrophobic portions can be in the range of about 5:1 to about 1:5, about 3:1 to about 1:3, about 2:1 to about 1:2, or about 1.5:1 to about 1:1.5. For example a (poly(butyleneterephthalate-co-ethylene glycol) copolymer with 45 wt. % polyethylene glycol (having an average molecular weight of 1000 kD) and 55 wt. % butyleneterephthalate, would have a weight ratio of hydrophilic portion to hydrophobic portion of about 1:1.22.

Typically, the hydrophilic/hydrophobic polymer comprises about 10% to about 50% weight of the basecoat layer.

In exemplary embodiments, the basecoat layer comprises a blend of poly(alkyl(meth)acrylate) (e.g., pBMA) and poly (ethylene-co-vinyl acetate) (pEVA). As an example, the polymers can be provided in a blend wherein the ratio of the first polymer (e.g., pBMA) to the second polymer (e.g., pEVA) is in the range of about 10:1 to about 10:1, about 4:1 to about 1:4, or more specifically in the range of about 1:1 to about 1:4.

In some aspects the basecoat layer further includes a hydrophilic/hydrophobic polymer such as a poly(ethylene glycol)-based block copolymer, for example, PEG/PBT polymers. Exemplary concentrations of the hydrophilic/hydrophobic polymer in the solvent can be in the range of up to 20 mg/mL, such as in the range of about 1 mg/mL to about 20 mg/mL.

Hydrophilic Bioactive Agents:

Coating systems of the invention comprise one or more hydrophilic bioactive agents that are present initially in the basecoat layer of the coating system. In exemplary embodiments, the hydrophilic bioactive agent is present in the basecoat layer in the form of microparticles.

In some aspects the hydrophilic bioactive agent is a macromolecule. Hydrophilic macromolecules are exemplified by compounds such as polypeptides, polynucleotides, and polysaccharides. The hydrophilic macromolecules can have a molecular weight of about 1000 Da or greater, 5,000 Da or greater, or 10,000 Da or greater.

In some specific aspects, the hydrophilic bioactive agent comprises a polypeptide. A polypeptide refers to an oligomer or polymer including two or more amino acid residues, and is intended to encompass compounds referred to in the art as proteins, polypeptides, oligopeptides, peptides, and the like. By way of example, peptides can include antibodies (both monoclonal and polyclonal), antibody derivatives (including diabodies, F(ab) fragments, humanized antibodies, etc.), cytokines, growth factors, receptor ligands, enzymes, and the like. Polypeptides can also include those that are modified with, or conjugated to, another biomolecule or biocompatible compound. For example, the polypeptide can be a peptide-nucleic acid (PNA) conjugate, polysaccharide-peptide conjugates (e.g., glyosylated polypeptides; glycoproteins), a poly(ethyleneglycol)-polypeptide conjugate (PEG-ylated polypeptides).

In some embodiments, the hydrophilic bioactive agents are polypeptides having a molecular weight of about 10,000 Da or greater, or about 20,000 Da or greater; more specifically in the range of about 10,000 Da to about 200,000 Da, or in the range of about 25,000 Da to about 75,000 Da.

In some embodiments, the hydrophilic bioactive agent includes antibodies and antibody fragments. A variety of antibody and antibody fragments are commercially available, obtainable by deposit or deposited samples, or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256: 495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD and any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

Examples of antibodies and antibody fragments include, but are not limited to, therapeutic antibodies include trastuzumab (Herceptin™), a humanized anti-HER2 monoclonal antibody (mAb); alemtuzumab (Campath™), a humanized anti-CD52 mAb; gemtuzumab (Mylotarg™), a humanized anti-CD33 mAb; rituximab (Rituxan™), a chimeric anti-CD20 mAb; ibritumomab (Zevalin™), a murine mAb conjugated to a beta-emitting radioisotope; tositumomab (Bexxar™), a murine anti-CD20 mAb; edrecolomab (Panorex™), a murine anti-epithelial cell adhesion molecule mAb; cetuximab (Erbitux™), a chimeric anti-EGFR mAb; bevacizumab (Avastin™), a humanized anti-VEGF mAb; Ranibizumab (Lucentis™), an anti-vascular endothelial growth factor mAb fragment, satumomab (OncoScint™) an anti-pancarcinoma antigen (Tag-72) mAb, pertuzumab (Omnitarg™) an anti-HER2 mAb, and daclizumab (Zenapax™) an anti IL-2 receptor mAb.

The polypeptide can also be selected from cell response modifiers. Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The polypeptide can also be selected from therapeutic enzymes, such as proteases, phospholipases, lipases, glycosidases, cholesterol esterases, and nucleases.

Specific examples include recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase.

Other bioactive agents that can be used for promoting a biological response, such as by altering gene function, include plasmids, phages, cosmids, episomes, integratable DNA fragments, antisense oligonucleotides, antisense DNA and RNA, modified DNA and RNA, iRNA (immune ribonucleic acid), ribozymes, siRNA (small interfering RNA), and shRNA (short hairpin RNA). Specific examples include antisense oligonucleotide against vascular endothelial growth factor (VEGF), such as MACUGEN™ (pegaptanib sodium) for the treatment of neovascular age-related macular degeneration (AMD).

Microparticles:

In some embodiments, the hydrophilic bioactive agent that is present in the basecoat layer is in the form of microparticles. The use of hydrophilic bioactive agent in the form of microparticles is advantageous as it allows for the preparation of coating systems with a desired distribution of bioactive agent in the system. The use of microparticles, in combination with the materials described herein, is also advantageous for the controlled release of bioactive agent. As yet another advantage, the microparticulate form can preserve bioactive agent activity because, in theory, within the microparticle the bioactive agent is not subject to the same structurally altering forces as it would be if it were simply solvated in the solvent or in an emulsion with the solvent.

Microparticles used with embodiments of the invention may be configured to provide a desired bioactive agent elution rate. The rate of bioactive agent elution from a microparticle will depend on various factors including the size of the microparticle, the presence or absence of other optional components in the microparticle such as a polymer, an additive, or a solvent, the erosion characteristics of the material in the microparticle, the structural features of the microparticle including porosity, overcoats and the like.

The term "microparticle" as used herein shall refer to non-dissolved particulate matter having a size of less than 1 mm in diameter (when observed as individual, discrete microparticles). The term "microparticle" also encompasses nanoparticles. In specific aspects, the basecoat layer includes a set of microparticles having an average diameter from about 10 nm to about 100 µm. In some more specifically aspects, the basecoat layer comprises a set of microparticles having an average diameters from about, from about 100 nm to about 25 µm, from about 500 nm to about 15 µm, or even more specifically from about 1 µm to about 10 µm. In an embodiment, microparticles are equal to or less than about 5 µm.

In some aspects of the invention, a microparticle set having a smaller average diameter is used to prepare the polymeric basecoat layer. The use of smaller diameter microparticles may improve control over release of the hydrophilic bioactive agent, such as in terms of rate and duration of release from the basecoat layer. The use of smaller diameter microparticles can also improve aspects of coating formation. For example smaller microparticles can provide smoother coatings and are also less likely to clog coating equipment. In some aspects the small microparticles have a diameter of less than about 10 µm.

In many aspects, the basecoat layer includes particles that are spherical or substantially spherical in shape. In a spherical particle, distances from the center (of the microparticle) to the outer surface of the microparticle will about the same for any point on the surface of the microparticle. A substantially spherical microparticle is where there may be a difference in radii, but the difference between the smallest radii and the largest radii is generally not greater than about 40% of the smaller radii, and more typically less than about 30%, or less than 20%.

The microparticle comprises a hydrophilic bioactive agent. The hydrophilic bioactive agent can have a solubility of at least 1 part agent per 50 parts water. In more specific aspects, the hydrophilic bioactive agent may be soluble (having a solubility of at least 1 part agent per from 10 to 30 parts water), freely soluble (having a solubility of at least 1 part agent per from 1 to 10 parts water), or very soluble (having a solubility of greater than 1 part agent per 1 part water). These descriptive terms for solubility are standard terms used in the art (see, for example, *Remington: The Science and Practice of Pharmacy*, 20$^{th}$ ed. (2000), Lippincott Williams & Wilkins, Baltimore Md.).

In many aspects of the invention, the microparticle is composed predominantly of, or entirely of, hydrophilic bioactive agent. For example, the microparticle polypeptide can include hydrophilic bioactive agent in an amount of about 90% wt or greater, about 95% wt or greater, about 98% wt or greater, or even about 99% wt or greater. This can be important in many therapeutic methods, as the amount of hydrophilic bioactive agent that is available to a subject following administration of the microparticles can be maximized.

In some preparations, the basecoat layer comprises microparticles composed predominantly of polypeptides. For example, polypeptide microparticles can be formed as described in commonly owned patent application U.S. Ser. No. 60/937,492, and entitled "Polypeptide Microparticles" (Slager et al.). Generally, these microparticles are formed in a solution, by coalescing polypeptides with a nucleating agent to form polypeptide nuclei; mixing a phase separation agent with the solution to further coalesce polypeptide around the polypeptide nuclei, thereby forming a mixture; cooling the mixture to form polypeptide microparticles; and removing all or part of the phase separation agent from the polypeptide microparticles. This method has been found to be particularly advantageous for the preparation of microparticles formed predominantly of antibody or antibody fragments, and provides microparticle sets having microparticles of desired sizes, with low size polydispersity, and which maintains good polypeptide activity.

Optionally, the microparticle can include a component that is different than the hydrophilic bioactive agent. The optional component can offer the advantage of providing additional control over the elution rate of the bioactive agent. In some embodiments, optional component can offer the advantage of increased protection of bioactive agent activity. This component can be a polymer, and can be distinct from the first and second polymer of the basecoat.

The optional polymer used with the microparticle can be degradable or non-degradable. A specific polymer can be selected based on various factors including compatibility with the bioactive agent, whether or not the polymer is degradable, speed and mode of erosion (bulk or surface), and compatibility or incompatibility with solvents used to apply the coating.

The polymer can be crosslinked in the particle, on the surface of the particle, or both. The polymer can include coupling groups, such as polymerizable groups, or reactive groups of a reactive pair (e.g., amine and amine-reactive groups) so that crosslinking can be established. A polymerization initiator can be included to promote crosslinking of polymers with polymerizable groups (macromers).

In an embodiment, the microparticle includes a degradable polymer. Elution of a bioactive agent from a particle including a degradable polymer can be from diffusion of the bioactive agent through the degradable polymer itself or through the erosion (bulk or surface erosion) of the degradable polymer. Degradable polymers can include those described in more detail below.

In some preparations, the microparticles include a natural biodegradable polysaccharide. The microparticle can be formed of a crosslinked matrix of natural biodegradable polysaccharide, with the hydrophilic bioactive agent within the crosslinked matrix. The microparticle can also have a coating or shell of crosslinked matrix of natural biodegradable polysaccharide. For example, the coating or shell can encompass a central core of bioactive agent. In this aspect, the central core can be a polypeptide microparticle as described above.

In some desired modes of practice, the biodegradable polysaccharide has a molecular weight of 500,000 Da or less, and includes pendent coupling groups (which allow for polysaccharide crosslinking). The pendent coupling groups can be in the form of polymerizable groups, or chemical groups forming a reactive pair (such as amine and amine-reactive groups). Exemplary biodegradable polysaccharides include amylose, maltodextrin, and polyalditol.

In some embodiments, the microparticles used are substantially monodisperse. In other embodiments, the microparticles used are polydisperse. In some applications, the use of substantially monodisperse microparticles is advantageous because elution rates from substantially monodisperse microparticles can be more consistent than release rates from otherwise similar polydisperse microparticles.

Microparticles having a characteristic elution rate can be combined with other microparticles having the same or a different characteristic elution rate. By combining particles with different characteristic release rates, the overall release rate of a bioactive agent from the particles and from the coating system that the particles are dispersed in can be manipulated as desired. For example, microparticles having a relatively fast elution rate can be combined in a coating with microparticles having a relatively slow elution rate to produce a composition elution profile that is desirable.

Optionally, one or more additional bioactive agents that are different than the hydrophilic bioactive agent can be present in the coating system. For example, one or more additional hydrophilic bioactive agents can be present in the microparticle, such as two different polypeptides.

The microparticles that are used in the composition can be formed in accordance with many different techniques, including those described or referred to herein, and known to those of skill in the art. The microparticles can be provided to the basecoat composition in dry (e.g., lyophilized form) or alternatively can be provided in a solvent used in the microparticle formation process.

The components of the coating composition can be added to the solvent in any particular order, or can be combined all at once. In many modes of practice the components are added with agitation to keep the microparticles dispersed.

In some modes of preparation, once the microparticles are produced or obtained, they are mixed with (a) a solvent and (b) at least the first polymer that will form the basecoat composition. An appropriate solvent, or solvent system, can be chosen for preparation of the composition. Different types of solvents can be used depending on the properties of the particles and the properties of the basecoat polymers. Suitable solvents include those that do not cause substantial or any dissolution of the microparticles during the process. Examples of solvents include toluene and xylene, ethers such as tetrahydrofuran; and amides such as dimethylformamide (DMF). Preferred solvents for use with polypeptide microparticles include halogenated alkanes such as methylene chloride and chloroform. Combinations of one or more of these or other solvents can also be used.

During basecoat formation, such as exemplified by a coating process, the composition (with the solids of the composition represented by the first polymer, microparticles, etc.) can be applied to a substrate, and then the solvent is allowed to evaporate from the surface. In some modes of practice, the composition may be prepared with the components (microparticles and polymer) at a low concentration, and the composition may be repeatedly applied to the surface build up the coating and increase the amount of solids. In some modes of practice, the composition may be prepared with the components (microparticles and polymer) at a higher concentration, and the composition applied once, or only a few times, to provide a coating with a desired amount of solids. As such, the method of forming the basecoat can be quite variable, and suited to provide a coating with desired characteristics, such as amount of bioactive agent, thickness, etc.

The amount of microparticles incorporated into the basecoat can be chosen based on various factors, including the type and amount of hydrophilic bioactive agent intended to be incorporated into the basecoat, and the desired release rate and duration of release of the bioactive agent from the basecoat. There is no particular lower limit of amount of microparticles to be dispersed in the basecoat composition.

Exemplary concentrations of microparticles dispersed in the solvent can be up to about 25 mg/mL, such as in the range of about 5 mg/mL to about 25 mg/mL, or more specifically in the range of about 10 mg/mL to about 15 mg/mL. In some aspects, the basecoat has an amount of microparticles (i.e., the amount of microparticles as a percentage of the total weight of the coating) of up to about 70% wt, in the range of about 30% wt to about 60% wt, about 30% wt to about 50% wt, or about 30% wt to about 40% wt.

The polymer components of the basecoat solution can be added to provide a concentration suitable for forming and holding the microparticles in place after the basecoat forms, and providing a basecoat layer with desired properties (e.g., elution properties). The total polymer concentration in the basecoat solution typically ranges from about 1 mg/mL to about 100 mg/mL, more typically ranging from about 1 mg/mL to about 60 mg/mL, or about 1 mg/mL to about 40 mg/mL.

In some embodiments the basecoat has an amount of total polymeric content (i.e., the amount of first polymer, second polymer, and hydrophilic/hydrophobic polymer as a percentage of the total weight of the basecoat composition) of greater than 30% wt, in the range of about 30% wt to about 70% wt, about 40% wt to about 70% wt, about 50% wt to about 70% wt, or about 60% wt to about 70% wt.

In one exemplary combination, the first polymer is a poly(alkyl(meth)acrylate), such as poly(n-butyl methacrylate) (pBMA), and the second polymer is poly(ethylene-co-vinyl acetate) (pEVA). As an example, the polymers can be provided in a blend wherein the ratio of the first polymer (e.g., pBMA) to the second polymer (e.g., pEVA) is in the range of about 10:1 to about 1:10, or in the range of about 4:1 to about 1:4. In an exemplary embodiment, the ratio of the first polymer to the second polymer is about 1:1.

In some embodiments the basecoat composition comprises a hydrophilic/hydrophobic polymer such as a poly(ethylene glycol)-based block copolymer. Exemplary concentrations of the hydrophilic/hydrophobic polymer in the solvent can be in the range of up to 20 mg/mL, such as in the range of about 1 mg/mL to about 20 mg/mL.

Elution-Controlling Topcoat Layer:

Coating systems of the invention comprise a topcoat layer that is applied over at least a portion of the basecoat layer. The topcoat layer acts to control the elution rate of the hydrophilic bioactive agent from the basecoat layer of the coating system. The topcoat layer comprises predominately poly(ethylene-co-vinyl acetate) copolymer ("pEVA") and may optionally include other polymers and optional ingredients. As used herein the term "poly(ethylene-co-vinyl acetate)" or pEVA" refers to copolymers that are produced by the copolymerization of ethylene ("E") with vinyl acetate ("VA"). Methods of making pEVA copolymers are well known to those of skill in the art.

Advantageously, it has been found that the vinyl acetate concentration in the pEVA topcoat layer can be used to control the elution rate of the hydrophilic bioactive agent from the basecoat layer of the coating system. More specifically, it has been found that as the concentration of vinyl acetate in the pEVA copolymer increases, the elution rate of the hydrophilic bioactive agent from the coating system also increases. Conversely, as the concentration of vinyl acetate in the pEVA decreases, the elution rate of the hydrophilic bioactive agent from the coating system also decreases. This relationship can be used in order to provide a coating system for an implantable medical article that has the desired elution rate of hydrophilic bioactive agent.

In many embodiments, the concentration of vinyl acetate in the pEVA topcoat layer ranges from about 10% to about 50% vinyl acetate, with the remainder of the copolymer comprising ethylene. pEVA copolymers having low amounts of vinyl acetate (e.g., less than about 10% VA) are quite insoluble in typically available solvents. This causes these low vinyl acetate pEVA copolymers to be difficult to coat, for example, using conventional solvent-based spray or dip coating techniques. pEVA copolymers having high amounts of vinyl acetate (e.g., greater than about 50% VA) suffer from durability problems due to their soft and non-crystalline nature. In many embodiments, the pEVA topcoat has a vinyl acetate concentration that ranges from about 15% to about 50% vinyl acetate, or from about 20% to about 35% vinyl acetate. Representative examples of useful pEVA copolymers include those having 12% vinyl acetate, 18% vinyl acetate, 25% vinyl acetate, 33% vinyl acetate, and 50% vinyl acetate.

In many embodiments, the molecular weight of the pEVA making up the topcoat layer ranges from about 40,000 to about 200,000 Da, more typically ranging from about 40,000 to about 120,000 Da or about 60,000 to about 100,000 Da.

In many embodiments, the pEVA topcoat layer comprises predominately pEVA, for example, greater than about 50% wt. pEVA polymer. Optionally, other components may be included in the pEVA topcoat, for example, pBMA and other alkyl methacrylate polymers, polystyrene, or polybutadiene. In many embodiments, the pEVA topcoat layer comprises about 50% wt. or greater pEVA, or about 60% wt. or greater pEVA, or about 70% wt. or greater pEVA, or about 80% wt. or greater pEVA, or about 90% wt. or greater pEVA, or about 95% wt. or greater pEVA, or about 99% wt. or greater pEVA.

An appropriate solvent, or solvent system, can be chosen for preparation of the topcoat composition. Different types of solvents can be used depending on the copolymer content in the pEVA copolymer. Suitable solvents include those that dissolve the pEVA copolymer and that are compatible with the basecoat layer (e.g., do not cause substantial or any dissolution of the microparticles during application of the topcoat). Representative examples of solvents include non-polar solvents such as heptane, hexane, toluene, chloroform, tetrahydrofuran (THF), dichloromethane, and the like. As the vinyl acetate concentration in the pEVA increases, more polar solvents may be suitable. Blends of two or more solvents can also be used.

Exemplary concentrations of the total polymer content in the topcoat composition can be in the range from about 1 mg/mL to about 100 mg/mL, more typically ranging from about 10 mg/mL to about 40 mg/mL, or from about 20 mg/mL to about 30 mg/mL.

In some aspects the topcoat composition is used to form a coating on a substrate such as an implantable medical device. The coating composition is then applied onto the substrate over the basecoat using any of a variety of coating techniques including dip-coating, spray-coating (including both gas-atomization and ultrasonic atomization), fogging, brush coating, press coating, blade coating, and the like. The topcoat composition may be applied under conditions where atmospheric characteristics such as relative humidity, temperature, gaseous composition, and the like are controlled.

In some embodiments, the topcoat composition is applied using a spray technique. Exemplary spray coating equipment that can be used to apply coatings of the invention can be found in U.S. Pat. Nos. 6,562,136; 7,077,910; 7,192,484; 7,125,577; U.S. Published Patent Applications 200610088653, and 2005/019424; and U.S. application Ser. Nos. 11/102,465 and 60/736,995.

During topcoat formation, the topcoat composition can be applied to a substrate having a previously applied basecoat, and then the solvent is allowed to evaporate from the topcoat. In some modes of practice, the composition may be prepared with the pEVA copolymer at a low concentration, and the topcoat composition may be repeatedly applied to the surface in order to build up the coating and increase the amount of solids. In some modes of practice, the composition may be prepared with the pEVA copolymer at a higher concentration, and the composition applied once, or only a few times, to provide a coating with a desired amount of solids. As such, the method of forming the topcoat can be quite variable, and suited to provide a coating with desired characteristics, such as amount of bioactive agent, thickness, and the like.

The coating system can have certain dimensions, such as thickness. In many aspects the thickness will be relatively uniform over the entire coating on the surface. In many embodiments, the thickness of the basecoat layer is greater than the diameter of the microparticles that may be present in the basecoat. For example, the thickness of the basecoat layer coating can be about 1 µm to about 200 µm, more typically ranging from about 1 µm to about 50 µm. In many aspects, the thickness of the topcoat layer can be selected to provide a desired elution rate of the hydrophilic bioactive agent from the coating system. For example, the thickness of the topcoat layer can be greater up to about 50 µm, more typically ranging from about 5 µm to 10 µm.

Devices:

Embodiments of the invention can be used to form elution-controlling coating systems for use in association with many different types of devices, including medical devices, including many different types of substrates. Medical devices can include both implantable devices (chronically and transiently implantable) and non-implantable medical devices. In many aspects, a composition used to form the coating system can be formed into a device as described herein.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuroaneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in connection with an ophthalmic device configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. No. 6,719,750 B2 ("Devices for Intraocular Drug Delivery," Varner et al.) and U.S. Pat. No. 5,466,233 ("Tack for Intraocular Drug Delivery and Method for Inserting and Removing Same," Weiner et al.); U.S. Patent Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. Patent Publication Nos. 2005/0276837 A1 (filed Dec. 15, 2005, Anderson et al.), 2004/0271706 A1 (filed Dec. 8, 2005, Anderson et al.), 20050287188 A1 (filed Dec. 29, 2005, Anderson et al.), 2008/0271703 A1 (filed Dec. 8, 2005, Anderson et al.), 2005/0281863 A1 (filed Dec. 22, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. Patent Publication No. 2006/0110428, filed Jul. 5, 2005, ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

The invention may be better understood with reference to the following examples. These examples are intended to be representative of specific embodiments of the invention, and are not intended as limiting the scope of the invention.

EXAMPLES

Example 1

Particle Preparation:

Non-specific Rabbit-IgG Fab-fragment (Fab, Southern Biotech) having the formulation: 70% protein, 30% trehalose, 0.1% Tween 20 (Brookwood Pharmaceuticals) were spray dried. Using Laser Diffraction (Sympatech) the particle size was determined to be $x_{10}=1.15$ μm, $x_{50}=2.35$ μm and $x_{90}=4.15$ μm.

Basecoat Preparation:

Basecoat 1 was prepared as follows: To 50 mg of the Fab spray-dried particles was added 625 μL of PolyActive™ polymer (55 wt. % 1000 molecular weight PEG and 45 wt. % PBT) @ 40 mg/ml in chloroform, 1.15 ml pBMA @ 40 mg/ml in chloroform, and 1.15 ml pEVA @ 40 mg/ml in chloroform. Additional chloroform was added until a volume of 5 ml was reached. The solution was homogenized in a sonic bath for 10 minutes prior to coating.

Basecoat 2 was prepared as follows: To 50 mg of the Fab spray-dried particles was added 1.56 mL of PolyActive™ polymer (55 wt. % 1000 molecular weight PEG and 45 wt. % PBT) @ 40 mg/ml in chloroform, 0.155 ml pBMA @ 40 mg/ml in chloroform, and 0.155 ml pEVA @ 40 mg/ml in chloroform. Additional chloroform was added until a volume of 5 ml was reached. The solution was homogenized in a sonic bath for 10 minutes prior to coating.

Topcoat Preparation:

pEVA topcoat solutions were prepared by dissolving pEVA polymer in chloroform at a concentration ranging from 10 mg/ml to 40 mg/ml dependent on solubility of the pEVA polymer.

Coating:

20 eye coil implants were coated (4 implants per group) with an average 1 mg basecoat deposition layer. The basecoat and topcoat formulations used for the coil implants are shown in TABLE 1. The resulting basecoat and topcoat used for each eye coil implant, coating weight, and Fab content are shown in TABLE 2.

TABLE 1

| | Fab Particles (% wt.) | PolyActive ™ (% wt.) | pEVA (% wt. (% VA)) | pBMA (% wt.) |
|---|---|---|---|---|
| Basecoat 1 | 30 | 15 | 27.5 (33% VA) | 27.5 |
| Basecoat 2 | 40 | 50 | 5 (33% VA) | 5 |
| Topcoat 1 | 0 | 0 | 100 (33% VA) | 0 |
| Topcoat 2 | 0 | 0 | 100 (18% VA) | 0 |

TABLE 2

| Basecoat Formulation | Basecoat Weight (mg) | Topcoat Formulation | Topcoat Weight (mg) | Fab (µg) |
|---|---|---|---|---|
| Basecoat 1 | 1.07 | None | 0 | 225 |
| | 1.13 | Topcoat 1 | 0.40 | 236 |
| | 1.14 | Topcoat 2 | 0.35 | 239 |
| Basecoat 2 | 1.03 | None | 0 | 289 |
| | 1.00 | Topcoat 2 | 0.35 | 279 |

Figure 1:
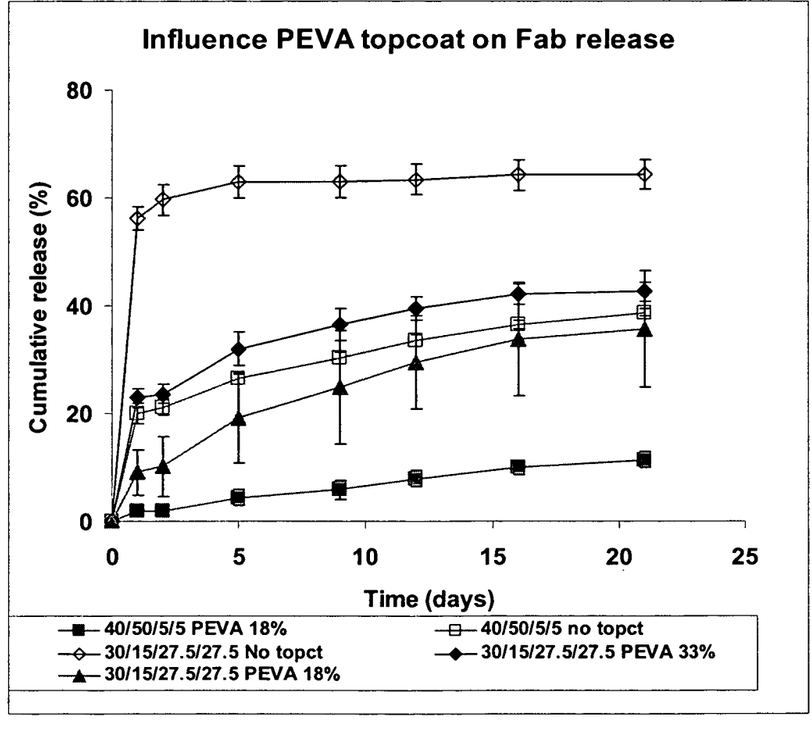
FIG. 1 is a graph displaying cumulative release of Fab (%) plotted as a function of time in days.

Testing:

After coating the resulting implants were dried in a nitrogen box overnight. The implants were put in wells of a 96-deep well plate adding PBS 1 ml to each well. The plate was placed on an orbital shaker at 37° C. At specific time intervals the elution medium was removed and analyzed for protein content and the fresh buffer was added to the implants. The cumulative release (%) is expressed as a function of the time (days) is shown in FIG. 1.

Example 2

Protein particles were prepared by lyophilizing a solution of protein in phosphate buffered saline (PBS). The dry material was then milled in chloroform until the protein solids were in the size range of about 1-2 microns. The milled protein particles were then suspended in chloroform at a concentration of 16.5 mg/ml.

Stock solutions of PolyActive™ polymer, pBMA and pEVA were prepared by dissolving the polymers into chloroform at 40 mg/ml. The PolyActive™ polymer comprised 55% PEG1000 and 45% butylene terephthalate. The pEVA had a vinyl acetate concentration of 33%.

A basecoat solution was prepared by first adding the PolyActive™ polymer stock solution to the protein suspension. Next, the pBMA and pEVA solutions were added. The total concentration of the resulting solution was then adjusted to 14 mg/ml by adding chloroform. The resulting basecoat solution had a composition comprising 30 wt. % protein particles, 15 wt. % PolyActive™ polymer, 27.5 wt. % pBMA, and 27.5 wt. % pEVA.

A topcoat solution was prepared by diluting the pEVA stock solution to 20 mg/ml in chloroform.

Eye coil implants were coated with the basecoat solution which resulted in the deposition of about 850 µg of dry basecoat. One half of the implants were then coated with the pEVA topcoat solution to provide a dry topcoat of 350 µg. The other half of the implants were not coated with a topcoat.

The implants were placed in PBS (pH 7.4, 37° C.) for protein elution measurements. A retained activity assay was used to measure the amount of protein release. The results are shown in TABLE 3. The top coat of PEVA 33% slowed and prolonged the release of the protein as compared to the no top coat controls.

TABLE 3

| Cumulative µg rabbit anti-goat Fab eluted from coating | | |
|---|---|---|
| Days | PEVA 33% VA (µg Fab) | No Top Coat (µg Fab) |
| 0 | 0 | 0 |
| 1 | 2.5 | 10 |
| 3 | 4 | 18 |
| 7 | 6.5 | 26 |
| 11 | 7.5 | 31 |
| 14 | 10 | 32 |
| 18 | 13 | 32.5 |
| 21 | 14.5 | 32.5 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A coating system comprising (a) a polymeric basecoat layer containing one or more hydrophilic bioactive polypeptides and a polymer comprising hydrophilic and hydrophobic portions; and (b) an elution-controlling topcoat layer that comprises 100% poly(ethylene-co-vinyl acetate) copolymer wherein vinyl acetate is present in an amount in the range of 12%-25% in the copolymer.

2. The coating system of claim 1, wherein vinyl acetate is present in an amount in the range of 12%-18% in the copolymer.

3. The coating system of claim 1, wherein vinyl acetate is present in an amount of 18% in the copolymer.

4. The coating system of claim 1, wherein the basecoat layer comprises (a) a first hydrophobic polymer; (b) the polymer comprising hydrophilic and hydrophobic portions; (c) optionally a second polymer; and (d) the hydrophilic bioactive agent.

5. The coating system of claim 4, wherein the hydrophilic bioactive agent is in the form of microparticles that are dispersed within the basecoat layer.

6. The coating system of claim 4, wherein the first hydrophobic polymer is a biostable polymer selected from the group consisting of poly(alkyl(meth)acrylates) and poly(aromatic(meth)acrylates).

7. The coating system of claim 4, wherein the first polymer is poly(n-butyl methacrylate) (pBMA).

8. The coating system of claim 4, wherein the second polymer comprises poly(ethylene-co-vinyl acetate) copolymer.

9. The coating system of claim 4, wherein the polymer comprising hydrophilic and hydrophobic portions is biodegradable polymer.

10. The coating system of claim 4, wherein the polymer comprising hydrophilic and hydrophobic portions comprises polyethylene glycol block copolymers and polyether ester copolymer.

11. The coating system of claim 4, wherein the polymer comprising hydrophilic and hydrophobic portions comprises PEG and PBT.

12. The coating system of claim 1, wherein the basecoat layer has a thickness ranging from about 1 μm to about 200 μm.

13. The coating system of claim 1, wherein the basecoat layer has a thickness ranging from about 1 μm to about 50 μm.

14. The coating system of claim 1, wherein the elution-controlling topcoat layer has thickness ranging up to about 50 μm.

15. The coating system of claim 1, wherein the elution-controlling topcoat layer has thickness ranging from about 5 μm to about 10 μm.

16. The coating system of claim 1, wherein the hydrophilic bioactive agent has a molecular weight of about 1000 Da or greater.

17. The coating system of claim 1, wherein the hydrophilic bioactive agent has a molecular weight ranging from about 10,000 Da to about 200,000 Da.

18. The coating system of claim 1, wherein the hydrophilic bioactive agent comprises a Fab fragment.

19. The coating system of claim 1, wherein the hydrophilic bioactive agent is soluble when dispersed within a solution comprising the base coat layer.

* * * * *